(12) United States Patent
Trese et al.

(10) Patent No.: US 6,207,066 B1
(45) Date of Patent: *Mar. 27, 2001

(54) METHOD FOR PURIFICATION OF A BLOOD COMPONENT

(75) Inventors: Michael T. Trese, Bloomfield Hills; George A. Williams, Grosse Pointe Park; Michael Hartzer, Rochester Hills; Wendelin A. Dailey, Lake Orion, all of MI (US)

(73) Assignee: Nuvue Technologies, L.L.C., NH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/178,970

(22) Filed: Oct. 26, 1998

Related U.S. Application Data

(63) Continuation-in-part of application No. 08/686,218, filed on Jul. 23, 1996, now abandoned.

(51) Int. Cl.[7] .......................... B01D 15/08; G01N 30/00; G01N 30/02; G01N 30/04
(52) U.S. Cl. .......................... 210/806; 210/656; 210/660; 210/669; 210/690; 210/782; 435/2; 435/217; 436/177; 436/523; 436/524; 530/412; 530/413; 530/417
(58) Field of Search ..................... 210/656, 660, 210/669, 690, 749, 767, 806, 782; 436/177, 178, 523, 524, 528; 530/412, 413, 415, 416, 417, 427, 830, 811; 435/2, 216, 217, 176; 502/405

(56) References Cited

U.S. PATENT DOCUMENTS

| | | | |
|---|---|---|---|
| 3,943,245 | 3/1976 | Silverstein | 424/101 |
| 4,356,958 * | 11/1982 | Kolobow et al. | 494/43 |
| 4,604,358 | 8/1986 | Fisher et al. | 435/217 |
| 4,724,207 * | 2/1988 | Hou et al. | 210/660 |
| 5,304,118 | 4/1994 | Trese et al. | 604/51 |
| 5,371,007 | 12/1994 | Linnau et al. | 435/217 |

OTHER PUBLICATIONS

Castellino and Powell (1981) Human Plasminogen Methods of Enzy., vol. 80, pp. 365–378.

* cited by examiner

*Primary Examiner*—John Kim
(74) *Attorney, Agent, or Firm*—Gifford, Krass, Groh, Sprinkle, Anderson & Citkowski, P.C.

(57) ABSTRACT

A method for rapid purification of a blood component from blood is described in which the blood plasma is first separated from the cellular blood elements by any conventional means, such as centrifugation. An affinity cartridge is then activated with a molecule, such as an amino acid, which binds with a blood component such as plasminogen. The separated blood plasma is then passed through the affinity cartridge such that the blood component is retained by the affinity cartridge. Thereafter, the blood component is eluted from the affinity cartridge by passing a buffer solution containing a releasing agent through the affinity cartridge. This releasing agent disengages the blood component from the affinity cartridge. The releasing agent is then separated from the eluted solution by passing the eluted solution through a device, such as an ion exchange or size exclusion device. The separated blood component, e.g. plasminogen, is then converted to plasmin by adding a known amount of an enzyme to the solution from which the releasing agent has been removed.

15 Claims, 1 Drawing Sheet

METHOD FOR PURIFICATION OF A BLOOD COMPONENT

CROSS-REFERENCE TO RELATED APPLICATIONS

This application is a continuation-in-part of U.S. Ser. No. 08/686,218 filed Jul. 23, 1996, abandoned.

FIELD OF THE INVENTION

The present invention relates to a method for the rapid purification of a blood component and, in particular, plasminogen which is then converted to plasmin.

DESCRIPTION OF THE PRIOR ART

There are many situations in which it is desirable to purify a particular blood component, such as plasminogen, from human blood. The separated blood component may then be broken down into further subcomponents, such as plasmin.

For example, our prior U.S. Pat. No. 5,304,118 which issued on Apr. 19, 1994, describes a method of injecting plasmin into a human eye in order to induce a posterior vitreous detachment. The plasmin is produced by adding an enzyme to plasminogen which is extracted from human blood.

For non-life-threatening surgical procedures, such as a vitrectomy utilizing plasmin injection, the risk of infection, such as AIDS infection, from unidentified whole blood sources is simply unacceptable. Consequently, it has been the previously known practice to extract blood from the patient in such non-life-threatening surgical procedures and then to extract the blood component, e.g. plasminogen, from the patient's own blood. Thus, even if such blood contains a viral infection, the reinjection of the blood component or subcomponent into the individual patient causes no harm.

In order to extract blood components such as plasminogen from blood, it has been the previous practice to utilize column chromatographic separation procedures. These types of columns are gravity fed and are open at the inlet. The flow rate through the column is limited by the force of gravity as well as the column dimensions. U.S. Pat. No. 3,943,245 to Silverstein discloses a method for purifying plasminogen from human and non-human mammalian plasma by modified affinity chromatography using Sepharose-L-lysine. The Sepharose-L-lysine is placed in a column which requires low flow rates through the column to prevent collapse of the column. U.S. Pat. No. 5,371,007 to Linnau et al. discloses a method of producing lys-plasminogen using a lysine-polyacrylamide gel as the matrix for affinity chromatography. However, both the method disclosed in Silverstein and the method disclosed in Linnau et al. utilized structurally weak materials for the affinity media which when utilized under high pressures collapse or create excessive back pressure. Furthermore, the Linnau et al. patent specifically seeks to provide a method for the large-scale isolation of plasminogen. While such procedures are effective, they are time consuming to perform, oftentimes requiring a full day or even more of laboratory time and require the use of pooled plasma. Fisher, Linnau et al., and Silverstein suggest an additional time consuming step by requiring that the plasma be extracted by stirring for two hours at 4° C. in phosphate buffer prior to the affinity chromatography. Castellino, *Methods of Enzy.*, Vol. 80, 265–377, 1981, calls for the removal of E-ACA from plasminogen by extensive dialysis against water at 4° C. This would require at least four additional hours and the use of a refrigerator. Linnau et al. suggest that for large scaled separations, the E-ACA could be removed by gel filtration or ion exchange chromatography. This would consist of packed columns containing weak column material which would require gravity feed, low pressure and a slow flow rate and thereby increasing separation time.

SUMMARY OF THE PRESENT INVENTION

The present invention overcomes the previously known disadvantages of the previously known blood component separation methods by providing a rapid separation and purification of a blood component utilizing the patient's own blood and which can be accomplished within a few minutes.

In brief, blood is first drawn from the patient and the blood plasma is separated from the cellular blood elements using conventional methods, such as centrifugation. After centrifugation, the blood plasma containing the blood component is retained and the cellular blood elements are discarded.

An affinity cartridge of the type which binds with the desired blood component is prepared prior to the time of use. L-lysine (or other protein binding component) is covalently attached to silica which has been epoxy activated. Silica is a material which can withstand very high pressure and still maintain its shape. This matrix yields low back pressure and high flow rates. Three mls of the lysine-silica is loaded into a cartridge and the lid is put on. The lid has a female luer-locked inlet to which a syringe can be attached. Liquids can be pushed through the cartridge with the use of a syringe at a rate which is up to ten times of that which could be achieved with the use of a gravity fed column.

A syringe containing equilibration buffer is attached to the cartridge and the buffer is pushed through it to pre-wet the cartridge. The syringe is discarded and replaced with a syringe containing plasma (normally 10 ml). The plasma is passed through the cartridge such that the desired blood component (PLGN) binds with the affinity cartridge and is removed from the plasma.

Thereafter, an affinity cartridge of the type which binds with the desired blood component is first washed with an equilibration buffer in order to activate the cartridge. The separated blood plasma is then passed through the affinity cartridge such that the desired blood component binds with the affinity cartridge and is effectively removed from the plasma. The plasma is then discarded.

Thereafter, an equilibration buffer is passed through the affinity cartridge to wash and remove any unbound proteins or the like that may be contained within the affinity cartridge. Upon completion of the washing step, only the bound blood component remains within the affinity cartridge.

The blood component is then eluted from the affinity cartridge by injecting an elution buffer containing a releasing agent. The releasing agent is selected such that the releasing agent frees or unbinds the blood component from the affinity cartridge. If desired, the releasing component (E-ACA) can be removed from the blood component by attaching an ion exchanging solid-phase extraction device to the outlet "out" of the affinity cartridge, prior to the blood component elution step. These devices consist of female luer inlets and male luer outlets. They contain strong supports which will not collapse when passing materials through them with an attached syringe. They do have limited capacity and could not be used for large scale separation purposes.

The elution buffer, releasing agent and blood component solution is then passed through an ion exchange cartridge. The ion exchange cartridge effectively removes the releasing agent and the eluted blood component is then collected within a sterile tube.

A known amount of an enzyme is then added to the eluted blood component to obtain the desired subcomponent, such as plasmin. The blood component or subcomponent is then used, optionally after further filtering, as desired in the surgical procedure.

BRIEF DESCRIPTION OF THE DRAWINGS

A better understanding of the present invention will be had upon reference to the following detailed description, when read in conjunction with the accompanying drawing, wherein like reference characters refer to like parts throughout the several views, and in which.

DETAILED DESCRIPTION OF A PREFERRED EMBODIMENT OF THE PRESENT INVENTION

The present invention will be described with respect to separating the blood component plasminogen from blood. The plasminogen is subsequently converted into plasmin and used for surgical procedures, such as a vitrectomy. It will be understood, of course, that other blood components may alternatively be separated from the blood utilizing the method of the present invention.

Figure 1:
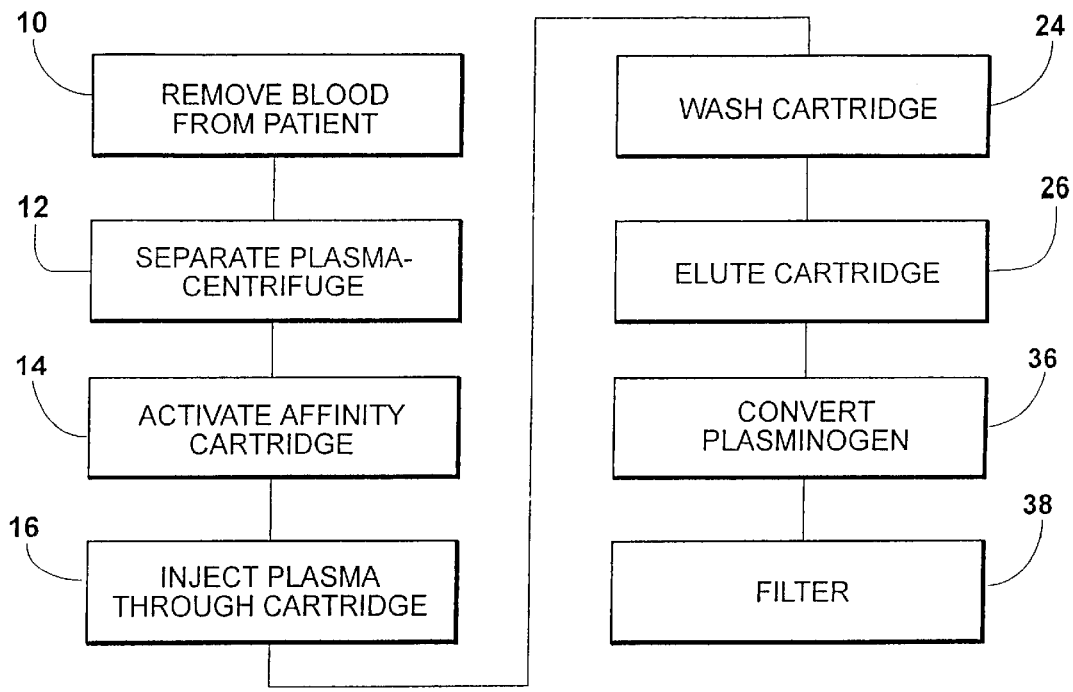
FIG. 1 is a process diagram illustrating the steps of the method of the preferred embodiment of the present invention.

With reference then to FIG. 1, at step 10 a predetermined amount of blood, for example 10 cc, is first removed from the patient in any conventional fashion such as by syringe containing an anticoagulant. The amount of blood removed from the patient will vary, of course, depending upon the final amount of the blood component required for the medical procedure.

At step 12, the blood plasma is separated from the cellular blood elements in any conventional fashion, such as by centrifuging. In the preferred embodiment of the invention, the blood is centrifuged at 1000 g for ten minutes at 5° C. The plasma is then collected in sterile syringes.

Figure 2:
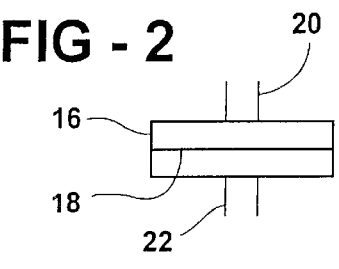
FIG. 2 is a side view illustrating an affinity cartridge.

With reference now to FIGS. 1 and 2, at step 14 (FIG. 1) an affinity cartridge 16 (FIG. 2) is washed and activated with an equilibration buffer solution. The affinity cartridge 16 includes a solid support 18 having an amino acid, such as L-lysine, affixed to it. The affinity cartridge also includes an luer inlet 20 and an outlet 22 such that all liquid injected into the inlet 20 passes through the solid support 18 and out through the outlet 22. After activating the affinity cartridge 16 with the equilibration buffer, the equilibration buffer is discarded.

The affinity cartridge 16 can contain 3 mls packed volume of affinity medium such as L-lysine bound to a rigid support such as epoxy-activated silica beads. Other alternative beads can include a ceramic matrix with lysine attached via a epoxy-activated linkage. The affinity media must be capable of withstanding the application of pressure necessary for performing rapid elution throughput without collapsing on itself The epoxy-activated silica beads are manufactured by Millipore Corporation, Waters Chromatography Division. They have a diameter of 40 μm, a pore size of 50 nm and a binding capacity of 3–7 μmoles of lysine per (ml) of packing material.

The lysine (L-lysine monohydrochloride, Sigma Chernical (L-6027) is then bound to the silica cartridge as follows: The silica beads are hydrated, the excess water is decanted. The beads are then incubated in coupling buffer (100 mM Na Phosphate, pH 8.0) for five minutes and the excess buffer is decanted. This is repeated two times. The lysine, solubilized in coupling buffer is then added to the beads in a 20 molar excess to the available binding sites on the silica beads and shaken in a water bath at 50° C. for five days. Following this, the unbound lysine is removed by decantation. The beads are then incubated in coupling buffer containing 1 M ethanolamine, pH 9.5 for 48 hours at 4° C. to block any unoccupied sites. The blocking solution is removed by decantation. The beads are then rinsed once with three volumes of coupling buffer, followed by four rinses with three volumes of 1 M NaCl and an additional rinse with three volumes of coupling buffer. The beads are stored in coupling buffer at 4° C.

The beads are packed into an empty Rezorian cartridge (Supelco). The cartridge is made of polypropylene with polyethylene frits. It has a luer lock fitting for syringe attachment.

An equilibration buffer containing primarily sodium phosphate can be used to activate the affinity cartridge 16. Approximately 10 cc or more of the equilibration buffer are passed through the affinity cartridge 16 during the activation step 14.

At step 16 the plasma separated at step 12 is injected into the inlet 20 of the affinity cartridge 16 so that the plasma passes through the solid support 18 and out through the cartridge outlet 22. In doing so, the blood component plasminogen reacts with the amino acid L-lysine and the plasminogen binds to the amino acid on the solid support 18 in the affinity cartridge. The plasma with the plasminogen removed is collected from the outlet port 22 of the cartridge 16 is then discarded.

At step 24 the cartridge containing the bound plasminogen is then washed to remove any unbound protein contained within the cartridge 16. Such washing is accomplished by passing approximately 48 cc of an equilibration buffer through the cartridge 16. The buffer which is injected through the cartridge 16 and is then discarded. In doing so, only the bound plasminogen remains attached to the affinity cartridge 16.

Figure 3:
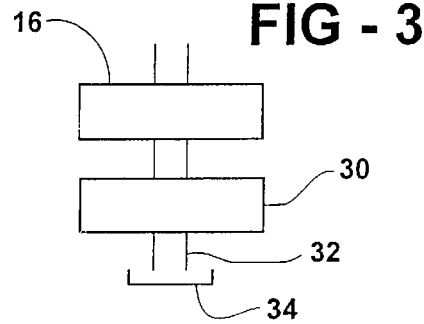
FIG. 3 is a side view of an affinity cartridge coupled with an ion exchange filter.
Figure 4:
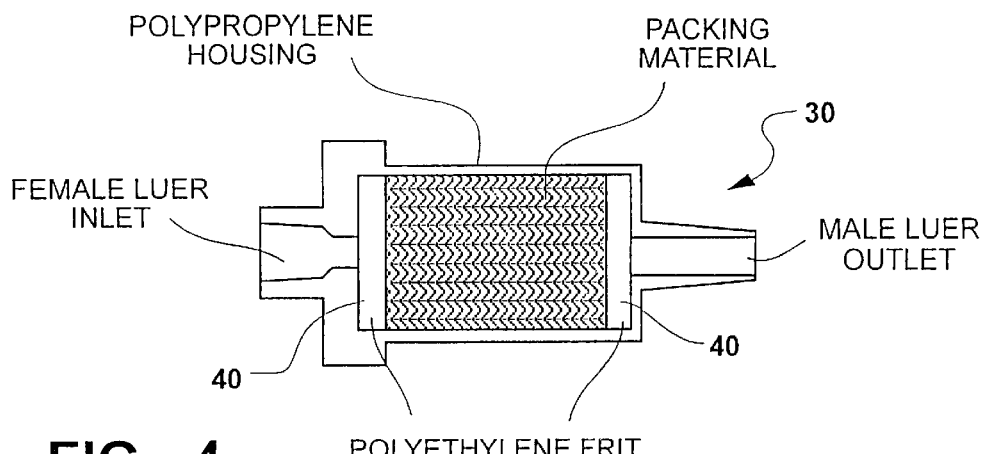
FIG. 4 is a side cross-sectional view of an ion exchange device of the present invention.

With reference now to FIGS. 1, 3, and 4, an ion exchange or size exclusion device 30 is coupled in series, e.g. with a Luer coupling, with the outlet port 22 from the affinity cartridge so that all solution passing through the cartridge 16 also passes through the ion exchange or size exclusion filter 30. A Maxi-Clean disk (Alltech Associates, Inc.) can include, for example, a solid-phase extraction device which consists of a high purity polystyrene-divinylbenzene cation exchange resin beads sandwiched between polyethylene frits 40 housed in a medical-grade polypropylene housing. At step 26 (FIG. 1) the plasminogen is then eluted from the affinity cartridge 16 by injecting a 2 cc solution of elution buffer containing a releasing agent, such as ε-amino-n-caproic acid. The releasing agent effectively releases the bound plasminogen from the affinity cartridge 16 so that the solution from the affinity cartridge contains elution buffer, the releasing agent and the blood component plasminogen.

Since the ion exchange or size exclusion device 30 is coupled in series with the affinity cartridge, the eluted solution of the elution buffer, releasing agent and plasminogen also passes through the ion exchange or size exclusion filter 30. The ion exchange or size exclusion device 30 binds with the releasing agent and effectively removes the releasing agent from the solution. Consequently, the filtered solution passing through the outlet port 32 of the ion exchange filter 30 contains only the elution buffer and the eluted plasminogen. This filtered solution is collected in a sterile tube 34 which may contain a known amount of enzyme 36, such as streptokinase. The enzyme effectively converts the plasminogen to plasmin at room temperature. pH is adjusted after conversation by addition of a know volume of sodium hydroxide.

Optionally, at step 38, the plasmin is sterilized by passing the plasmin through a filter, such as a 0.22 micron filter such as a Corning 21032-13 assembly containing a cellulose acetate membrane in a polypropylene housing, prior to use. If any delay is required before the plasmin is to be used, it should be stored at lower temperatures until required.

The above-described separation of the blood component plasminogen and its subsequent conversion into plasmin can be accomplished in the matter of a few minutes in the operating room. The present invention can also include a kit for rapid purification of plasmin from human plasma. The kit can include a syringe, a lysine affinity cartridge, a cation exchanger, a filter adapted to be attached to a syringe (i.e., 0.22 μm), and suitable buffers and reagents necessary for separating and purifying plasmin.

EXAMPLE

A kit, as described above, designed for the rapid purification and activation of autologous plasmin was utilized. Blood is drawn into 3 yellow capped (ACD) tubes which can be supplied as part of the kit. The tubes containing the blood are centrifuged at 750×g for fifteen minutes to obtain plasma separation. A sterile 21 ga needle can be attached to a 10 cc syringe (Syringe A), the needle inserted through the cap of the blood collection tube and the plasma aspirated. This step can be repeated for the second and third tubes until 10 cc of plasma are collected in Syringe A. All syringes are sterile medical grade syringes.

The cation exchange disk can be pre-wetted by attaching a 10 cc syringe containing sterile water to the ion exchange device and injecting the contents of the syringe through the device. The water is then discarded and the cation exchange device can be set aside until the preactivation step.

The affinity cartridge is then attached to the end of syringe A and the plasma is then injected slowly through the cartridge to allow the plasminogen to bind to the cartridge. The syringe may then be discarded.

The affinity cartridge is then attached to a 60 cc syringe (Syringe B) containing 40 cc of sterile 100 mM Na phosphate, pH 8.0. The buffer is injected through the cartridge to remove any unbound material from the affinity cartridge. For optimum recovery it is essential to wait until dripping from the end of cartridge has completed ceased before proceeding to the next step. The syringe can then be removed and discarded.

The cation exchange disk can be preactivated by attaching a 3 cc syringe (Syringe C) containing 1.2 cc sterile 15 mM ε-amino caproic acid (AMICAR, American Reagent Laboratories) in 100 mM Na phosphate, pH 8.0 to the disk and injecting the contents of the syringe through the disk.

The affinity cartridge can the be attached to a 10 cc syringe (Syringe D) containing 2 cc of sterile 15 mM ε-amino caproic acid (AMICAR, American Reagent Laboratories) in 100 mM Na phosphate, pH 8.0. The contents of Syringe D are then injected through the cartridge and discarded.

The cation exchange device is then attached to the end of the affinity cartridge and the sterilization filter can then be attached to the free end of the cation exchange device. The assembled unit is then attached to the end of Syringe E. The contents of Syringe E (1 cc of sterile 100 mM Na phosphate, pH 8.0 and 15 mM ε-amino caproic acid (AMICAR, American Reagent Laboratories) is then injected through the assembly. This solution is used to elute the plasminogen from the affinity cartridge. The cation exchange filter is then used to remove the ε-amino caproic acid from the eluant. The plasminogen is then collected in a sterile vial which contains 50,000 IU of sterile streptokinase (Kabikinase, KabiVitrum) and sodium phosphate buffer, pH 7.3. The vial is then gently agitated and 10 minutes to allow for the conversion of plasminogen to plasmin.

To confirm that active plasmin is present, a drop of plasmin can be placed in a well of a microtiter plate which contains a synthetic substrate (D-val-leu-lys-PHA, Sigma (V-0882). Cleavage of the substrate produces a bright yellow color which can be compared to an enclosed standard.

The plasmin is now ready for use such as for injection into the eye.

It will, of course, be understood that different blood components utilizing different binding agents and different releasing agents may alternatively be used without deviation from the spirit or scope of the present invention.

Having described our invention, many modifications thereto will become apparent to those skilled in the art to which it pertains without deviation from the spirit of the invention as defined by the scope of the appended claims.

We claim:

1. A method for rapid purification of plasminogen from blood comprising the steps of:

centrifuging blood plasma from cellular blood elements;

activating an affinity cartridge of the type which binds with plasminogen, said affinity cartridge containing affinity media selected from the group consisting of silica and ceramic matrix having a solid support and a molecule disposed thereon having affinity for the plasminogen;

passing the centrifued blood plasma through the affinity cartridge without prior solvent extraction of blood plasma so that the plasminogen is retained by the affinity media, the affinity media having a solid support which can withstand high pressure and a molecule disposed thereon having affinity for the plasminogen;

thereafter eluting the plasminogen from the affinity cartridge by passing a releasing agent through the affinity cartridge, the releasing agent disengaging the plasminogen from the affinity cartridge; and thereafter separating the releasing agent from the solution containing both the eluted releasing agent and the plasminogen.

2. The invention as defined in claim 1 and further comprising the step of converting said plasminogen following said separation of the releasing agent.

3. The invention as defined in claim 2 wherein said converting step comprises the step of introducing an enzyme to the plasminogen.

4. The invention as defined in claim 1 wherein the affinity media comprises L-lysine.

5. The invention as defined in claim 1 wherein the solid support comprises silica beads.

6. The invention as defined in claim 1 wherein a syringe can be attached to the affinity cartridge.

7. The invention as defined in claim 5 wherein the L-lysine is covalently attached to the silica beads by a epoxy linkage.

8. The invention as defined in claim 1 wherein the releasing agent comprises ε-amino-n-caproic acid.

9. The invention as defined in claim 1 wherein separating the releasing agent from the solution comprises the step of passing the releasing agent and plasminogen solution through an ion exchange or size exclusion filter which removes the releasing agent from the releasing agent and plasminogen solution.

10. The invention as defined in claim 1 wherein separating the releasing agent from the solution further comprises the step of passing the releasing agent and plasminogen solution through an ion exchange or size exclusion device whereby the releasing agent is removed from the solution containing plasminogen and releasing agent.

11. The invention as defined in claim 10 wherein the ion exchange or size exclusion device comprises a rigid support which can withstand the pressure produced by syringe injection.

12. The invention as defined in claim 3 wherein said enzyme converts the plasminogen to plasmin.

13. The invention as defined in claim 12 wherein the enzyme comprises streptokinase.

14. The invention as defined in claim 1 wherein the affinity media contains a molecule selected to bind with the plasminogen.

15. A method for rapid purification of plasminogen from blood comprising the steps of:

activating an affinity cartridge of the type which binds with plasminogen;

passing blood plasma through the affinity cartridge without prior solvent extraction of blood plasma so that the plasminogen is retained by the affinity cartridge, the affinity cartridge comprising an affinity media selected from the group consisting of silica and ceramic matrix having a solid support and a molecule disposed thereon having affinity for the plasminogen;

thereafter eluting the plasminogen from the affinity cartridge by passing a releasing agent through the affinity cartridge, the releasing agent disengaging the plasminogen from the affinity cartridge; and thereafter filtering the releasing agent from the eluted releasing agent and plasminogen solution.

\* \* \* \* \*